US00PP19226P3

(12) United States Plant Patent
Stemkens

(10) Patent No.: US PP19,226 P3
(45) Date of Patent: Sep. 16, 2008

(54) *VERBENA* PLANT NAMED 'REDANA'

(50) Latin Name: *Verbena×hybrida*
Varietal Denomination: Redana

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/641,146

(22) Filed: Dec. 18, 2006

(65) Prior Publication Data

US 2008/0148442 P1 Jun. 19, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—S. B. McCormick-Ewoldt
(74) *Attorney, Agent, or Firm*—S. Matthew Edwards

(57) ABSTRACT

A new *Verbena* plant particularly distinguished by its deep red flower, early flowering, and a habit that is upright and later spreading.

1 Drawing Sheet

Latin name of the genus and species of the plant claimed: *Verbena×hybrida.*
Varietal denomination: 'Redana'.

BACKGROUND OF THE NEW PLANT

The present invention comprises a new distinct cultivar of *Verbena,* botanically known as *Verbena ×hybrida.*

The new cultivar originated from a branch mutation of 'Scarlena.' This mutation was discovered in the field. 'Scarlena' is commercially available and is known by the synonym 'Tukana Scarlet.' 'Scarlena' has been patented as U.S. Plant Pat. No. 12,578.

As a result of this mutation the present cultivar was created in 2002 in Enkhuizen, Netherlands and has been repeatedly asexually reproduced by cuttings in Enkhuizen, Netherlands and Sarrians, France over a two year period. The new variety is stable and reproduces true to type in successive generations of asexual reproduction.

This new *Verbena* plant is an annual in most climatical zones in the US, only in zones 8, 9 and 10 it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena.* The data that define these characteristics were collected from asexual reproductions carried out in Enkhuizen, Netherlands. The plant history was taken on 14 weeks old plants, blossomed under natural light in a greenhouse, and grown in a 10.5 cm container. Color readings were taken in the greenhouse under ambient light.

Color references are primarily to the R.H.S. Colour Chart of The Royal horticultural Society of London.

TABLE 1

DIFFERENCES BETWEEN THE NEW CULTIVAR 'REDANA' AND ITS PARENT

| | 'Redana' | 'Scarlena' (U.S. Plant Patent No. 12,578) |
|---|---|---|
| Flower color | Dark red | Scarlet |
| Flower size | 15-17 mm | 17-19 mm |
| Seed set | Little | No |

The plant:

*Classification.*—Botanical : *Verbena×hybrida.*
*Parentage.*—Branch mutation of 'Scarlena,' U.S. Plant Pat. No. 12,578.
*Growth habit.*—Upright, decumbent.
*Plant height.*—15–20 cm.
*Spreading area of plant.*—50–70 cm.
*Branching character.*—Freely branching and lateral branching at every node.
*Number of branches per plant.*—24–34.
*Blooming period.*—From March until November.

The stem:

*Diameter.*—2 mm.
*Length.*—14–24 cm.
*Shape.*—Tetragonal.
*Anthocyanin pigmentation.*—Absent.
*Color of the stem.*—146A.
*Length of internode.*—20–60 mm.
*Texture.*—Smooth.
*Pubescence.*—Pubescent.
*Length lateral branches.*—40–55 cm.

The foliage:

*Phyllotaxis.*—Opposite.
*Shape of blade.*—Broadly ovate.
*Texture.*—Upper side : Smooth. Lower side : Smooth.
*Venation.*—Pinnate.
*Leaf margin.*—Dentate.
*Leaf base.*—Obtuse.

*Leaf apex.*—Acute.
*Length.*—32–46 mm.
*Width.*—24–36 mm.
*Depth of incision.*—3–5 mm.
*Number of incisions.*—12–20 per leaf.
*Colour.*—Upper side 137A. Lower side : 141B.
*Pubescence.*—Slightly pubescent.
*Length of petiole.*—2 mm.
*Petiole surface structure.*—Slightly pubescent.
*Petiole diameter.*—1 mm.
*Petiole coloration.*—141B, both surfaces.

The bud:
*Peduncle length.*—40–60 mm.
*Peduncle diameter.*—2.5 mm.
*Peduncle color.*—137B.
*Bud size.*—Diameter : 2 mm. Length : 4–6 mm.
*Bud shape.*—Elongated and ovate.
*Bud color.*—47C.
*Sepals.*—Color (upper side) : 137B. Color (lower side) : 137B. Form : Upright. Number : 5, fused. Length : 6–8 mm. Width : 2 mm. Shape : Elongated. Apex : Emarginate. Base : Fused. Margin : Entire.

The flower:
*Flower diameter.*—15–17 mm.
*Flower height.*—14–22 mm.
*Flower tube length.*—14–22 mm.
*Flower throat diameter.*—2 mm.
*Flower throat colour.*—156B.
*Inflorescence.*—Corymb.
*Flower.*—Form : Single, salverform; sessile on terminal corymbs.
*Petal color.*—Upper side : From 53A in the center to 46B on the edge. Lower side : 46C.
*Overlapping of petals.*—Separate.
*No. of petals.*—Gamopetalous, 5 lobed.
*Petal apex.*—Obcordate.
*Petal base.*—Fused.
*Petal margin.*—Entire.
*Petal surface texture.*—Smooth.
*Size of the petal.*—Length : 6–8 mm. Width : 4–6 mm.
*Inflorescence.*—Length : 20–40 mm. Diameter : 40–60 mm.
*Calyx length.*—7–9 mm.
*Calyx diameter.*—3 mm.
*Anthocyanin pigmentation of calyx limb.*—Absent.
*Color of the calyx.*—137C.
*No. of flowers per inflorescence.*—201–35.
*Fragrance.*—No fragrance.
*Bloom time of one inflorescence.*—New florets continue to open in one corymb over a period of 15 days.
*Lastingness of one flower.*—2–4 days.

Reproductive organs:
*Androecium.*—Stamens quantity : 4. Anther shape : Ovoid. Anther length : 1 mm. Anther color : 144B. Pollen amount : No pollen.
*Gynoecium.*—Pistils quantity : 1. Pistil length : 1–1.5 cm. Stigma shape : Bi-lobed. Stigma color : 144C. Style length : 1.9 cm. Style color : 144C. Ovary color : 144C.

The fruit and the seed:
*Seed set.*—Little fruit-development and seed-set has been observed.
*Seed shape.*—Elongated.
*Length.*—4 mm.
*Width.*—1 mm.
*Color.*—166B.

Roots:
*Type of roots.*—Fibrous, color 155B. Roots start to grow on every part of the stem that contacts the soil, so not only at the nodes.

Physiological and ecological characteristics

Disease/pest resistance: Plants of the new *Verbena* have been noted to be resistant to especially powdery mildew.

Temperature tolerance: Plants of the new *Verbena* have been observed to tolerate temperatures from −2–35 degrees C.

What is claimed is:

1. A new and distinct variety of *Verbena* plant, substantially as herein illustrated and described.

* * * * *

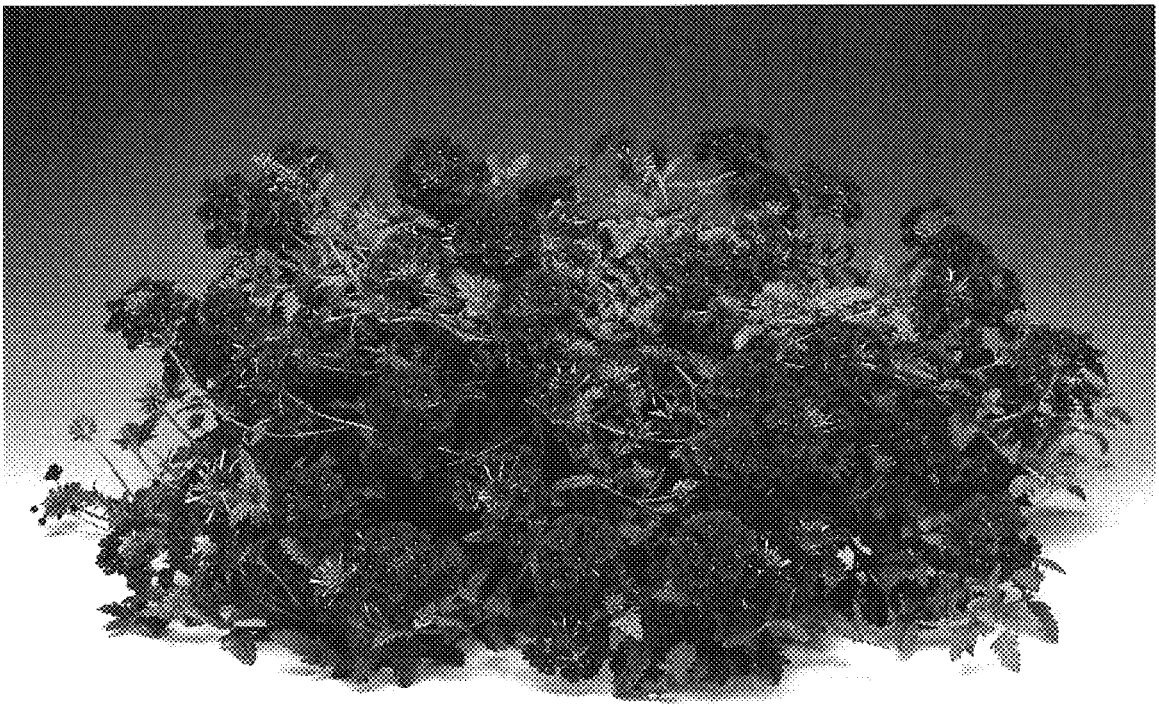

UNITED STATES PATENT AND TRADEMARK OFFICE

CERTIFICATE OF CORRECTION

PATENT NO. : PP 19,226 P3
APPLICATION NO. : 11/641146
DATED : September 16, 2008
INVENTOR(S) : Henricus G. W. Stemkens It is certified that error appears in the above-identified patent and that said Letters Patent is hereby corrected as shown below:

At column 1, line 38, delete “weeks” and insert therefor --week--

At column 4, following “No. of flowers per inflorescence .-”, delete “201-35” and insert therefor --20-35--

Signed and Sealed this

Eleventh Day of November, 2008

JON W. DUDAS
*Director of the United States Patent and Trademark Office*